United States Patent
Kartoun et al.

(10) Patent No.: US 11,348,680 B2
(45) Date of Patent: May 31, 2022

(54) SYSTEM FOR ASSIGNMENT OF ASSESSMENT TASKS BASED ON TASK CRITERIA AND REVIEWER CREDENTIALS

(71) Applicant: International Business Machines Corporation, Armonk, NY (US)

(72) Inventors: Uri Kartoun, Cambridge, MA (US); Tanya Rudakevych, Boston, MA (US); Charalambos Stavropoulos, Hastings-on-Hudson, NY (US); Sophie Batchelder, Lancaster, PA (US); Veronica Aldous, Davie, FL (US); Michael J. LaScaleia, Sudbury, MA (US); Francis Campion, Westwood, MA (US); Kenney Ng, Arlington, MA (US)

(73) Assignee: International Business Machines Corporation, Armonk, NY (US)

( * ) Notice: Subject to any disclaimer, the term of this patent is extended or adjusted under 35 U.S.C. 154(b) by 214 days.

(21) Appl. No.: 16/433,486

(22) Filed: Jun. 6, 2019

(65) Prior Publication Data
US 2020/0388378 A1 Dec. 10, 2020

(51) Int. Cl.
*G16H 40/20* (2018.01)
*G06N 20/00* (2019.01)
*G16H 10/60* (2018.01)

(52) U.S. Cl.
CPC ............ *G16H 40/20* (2018.01); *G06N 20/00* (2019.01); *G16H 10/60* (2018.01)

(58) Field of Classification Search
CPC ........ G16H 10/60; G16H 50/20; G16H 10/20; G16H 40/20; G16H 20/30
See application file for complete search history.

(56) References Cited

U.S. PATENT DOCUMENTS

| 8,924,236 B2 | 12/2014 | Marchosky |
| 9,679,107 B2 | 6/2017 | Cardoza et al. |

(Continued)

FOREIGN PATENT DOCUMENTS

| WO | 2015074062 A1 | 5/2015 | |
| WO | 2017070255 A1 | 4/2017 | |
| WO | WO-2018044872 A1 * | 3/2018 | .......... G06F 19/321 |

OTHER PUBLICATIONS

South, Brett Ray. Evaluating the effects of noninteractive and machine-assisted interactive manual clinical text annotation approaches on the quality of reference standards. The University of Utah, 2014. (Year: 2014).*

*Primary Examiner* — Jason B Dunham
*Assistant Examiner* — Constantine Siozopoulos
(74) *Attorney, Agent, or Firm* — Troutman Pepper Hamilton Sanders LLP (57) ABSTRACT

A system and method for assigning assessment tasks includes determining tasks in need of completion, where the tasks include assessing a set of documents containing medical patient data and providing a judgment (e.g., classification or label) based on the contents of the document. A process also includes selecting one or more reviewers based on the one or more tasks and providing one or more documents from the set of documents to each of the selected one or more reviewers for completion of the one or more tasks. The process further includes receiving a result of the one or more tasks after completion by the selected one or more reviewers and storing the result in an electronic medical record database.

19 Claims, 4 Drawing Sheets

(56) References Cited

U.S. PATENT DOCUMENTS

| | | | |
|---|---|---|---|
| 9,740,665 B2 | 8/2017 | Riskin et al. | |
| 2013/0080187 A1* | 3/2013 | Bacon | G16H 70/60 |
| | | | 705/3 |
| 2016/0048655 A1* | 2/2016 | Maitra | G16H 20/10 |
| | | | 705/3 |
| 2017/0018020 A1* | 1/2017 | Zhou | G16H 10/60 |
| 2019/0130073 A1* | 5/2019 | Sun | G06N 7/005 |
| 2019/0326000 A1* | 10/2019 | Bao | G16H 10/60 |

* cited by examiner

SYSTEM FOR ASSIGNMENT OF ASSESSMENT TASKS BASED ON TASK CRITERIA AND REVIEWER CREDENTIALS

TECHNICAL FIELD

The present application relates to an assessment system and, more particularly, to a system for assignment of assessment tasks based on task criteria and reviewer credentials.

BACKGROUND

Disease diagnosis and medical condition assessment is, in general, a subjective judgment based on the knowledge and expertise of a reviewing physician. The physician reviews relevant factors, takes notes, makes observations, and documents patient encounters as part of the patient's medical record. Electronic medical records (EMRs) are data elements that are captured for all patients, including laboratory values, diagnoses, medications, and demographic details. Often a patient's record is associated with a variety of data elements; such data elements are commonly stored either in a structured form (in a table) or as an unstructured form (narrative text). The two data types complement each other and provide together a comprehensive overview of the patient's current condition and medical history. EMRs are widely used and serve as the main data source in many scientific studies and applications, as they contain highly detailed information to understand medical outcomes.

When an academic investigator or a commercial company wishes to develop a classification or a prediction algorithm applied on a very large collection of EMRs they often encounter a major challenge of lacking accurate classifications or labels of the desired predicted outcome (e.g., medical condition). For instance, insomnia is known as an under-documented disease and thus the presence of a diagnosis code for insomnia in an EMR may not necessarily be a sufficient indication of the population of people that experience insomnia. Furthermore, often an insomnia medication is prescribed to treat a condition other than insomnia (e.g., anxiety), so a prescription for insomnia found in the patient's EMR does not necessarily provide indication that the patient actually has the condition.

When the classification of an ambiguously-documented disease is needed, it is common to assign a physician or a nurse to perform a manual chart review and classify each patient as having or not having the condition. The classifications extracted from the patient's records along with the physician's classifications can then be used to perform more reliable data analytics. For example, the manually-classified charts may be used as ground truth to train a machine learning algorithm for automated classification of a medical condition.

The present disclosure is directed towards addressing this and other shortcomings of the prior art.

SUMMARY

In some embodiments, a computer-implemented method for assigning assessment tasks through an assignment system including a processing device and a memory storing instructions which are executed by the processor is disclosed. The method includes determining one or more tasks for assessing a set of documents containing medical patient data, selecting one or more reviewers based on the one or more tasks, providing one or more documents from the set of documents to each of the selected one or more reviewers for completion of the one or more tasks, receiving a result of the one or more tasks after completion by the selected one or more reviewers, and storing the result in an electronic medical record database.

In other embodiments, a task assignment system is disclosed. The task assignment system includes a tasking system configured to receive a task request for the review of a set of documents containing patient medical data. The task request includes a task to label the documents containing patient medical data and acceptable label values. The task assignment system further includes a reviewer selection system configured to select one or more reviewers from a pool of reviewers to complete the task and provide one or more documents from the set of documents to each of the selected one or more reviewers for completion of the task. The task assignment system also includes a results system configured to receive a result of the one or more tasks after completion by the selected one or more reviewers and store the result in an electronic medical record database.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION OF EXEMPLARY EMBODIMENTS

Embodiments of the present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a head disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network (LAN), a wide area network (WAN) and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object-oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including LAN or WAN, or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operations steps to be performed on the computer, other programmable apparatus, or other device to produce a computer implemented process, such that the instructions which execute on the computer, other programmable apparatus, or other device implement the functions/acts specified in the flowcharts and/or block diagram block or blocks.

The flowcharts and block diagrams in the Figures illustrate the architecture, functionality, and operation of possible implementations of systems, methods, and computer program products according to various embodiments of the present invention. In this regard, each block in the flowcharts or block diagrams may represent a module, segment, or portion of instructions, which comprises one or more executable instructions for implementing the specified logical functions. In some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts or carry out combinations of special purpose hardware and computer instructions.

The present disclosure relates to a system and method for assigning assessment tasks to one or more reviewers and storing feedback as part of an EMR. An assignment system may split a plurality of tasks between a plurality of reviewers such that the tasks are completed efficiently and effectively. In one example, the assignment system divides medical documentation between qualified reviewers for the purpose of receiving an assessment from the reviewer regarding whether a medical condition is present based on the medical documentation.

In some embodiments, the assignment system further receives results from assigned tasks and stores these results as part of an EMR. For example, the assignment system may receive a classification of a medical condition from the reviewer based on the reviewer's analysis of the medical documentation and store the classification as part of the associated patient's medical record (or an anonymized record). These classifications may be used in combination with other medical record data to train a machine learning algorithm to automatically perform the classification task on additional documents, serving as an alternative to a manual review performed on the additional documents.

In some embodiments, the assignment system is configured to consider reviewer credentials in selection of reviewers and/or in consideration of the result of the reviewers' analysis. For instance, the assignment system may review expertise data related to the reviewer before determining whether to assign a particular task to that individual. This feature helps prevent unqualified reviewers from being assigned certain tasks. Moreover, the most qualified reviewers may be appropriately assigned to tasks that match their expertise and thus can be expected to produce reliable results. Further, due to the intensive nature of some manual review tasks, it may be unreasonable to only assign the tasks to the most qualified reviewers. In order to address this issue, results may be weighted with a confidence score based on the expertise of the reviewer in order to rely more heavily on certain results without burdening those reviewers with all of the tasks.

Figure 1:
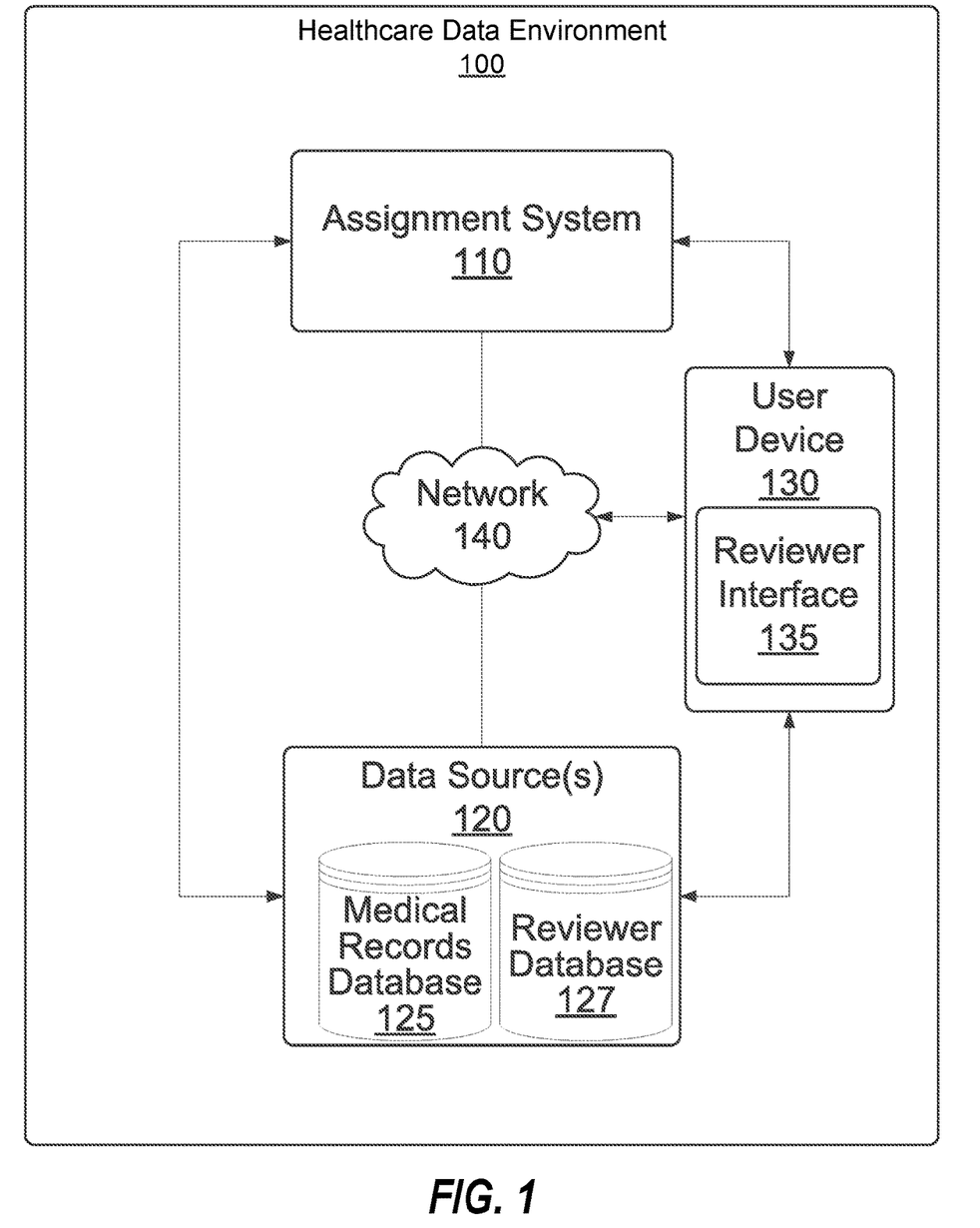
FIG. 1 is a block diagram of an example healthcare data environment, according to an embodiment.

FIG. 1 is an illustration of an exemplary healthcare data environment 100. The healthcare data environment 100 may include assignment system 110, one or more data sources 120 having a medical records database 125 and a reviewer database 127, and a user device 130 having a reviewer interface 135. A network 140 may connect the assignment system 110, the one or more data sources 120, and/or the user device 130.

The assignment system 110 may be a computing device. The assignment system 110 may include components that enable disclosed functions for assigning tasks to reviewers. The assignment system 110 may include a processing device and a memory, for example. The assignment system 110 is configured to execute instructions stored in the memory through the processing device to perform a task assignment method.

The one or more data sources 120 may be computing devices and/or storage devices configured to supply data to the assignment system 110 and/or the user device 130. For example, the one or more data sources 120 may include the medical records database 125 storing medical documentation. The medical records database 125 may include patient medical details (such as labs, procedures, comorbidities). Additionally, the medical records database 125 may also include progress reports, office visit summaries, prescription order details, discharge summaries, among other types of documentation associated with the patients. The medical records database 125 may include clinical narrative notes, including any narrative content or notes entered by a user with regard to a patient's health. In an exemplary embodiment, the medical records database 125 may include EMRs (associated with patients or anonymized). The EMR may include one or more documents containing medical data. In some embodiments, the medical records database 125 may comprise a corpus of documents containing medical data. The documents containing medical data may include any type of documentation, whether electronic, hard copy scans, location data for hard copies of documents, etc., including patient charts, clinical narrative notes, tables, test results, images, and the like.

The one or more data sources 120 may also include the reviewer database 127 which may include reviewer information for a plurality of potential reviewers. The reviewer database 127 may include data associated with expertise information for the plurality of reviewers. For example, the reviewer database 127 may store at least the names of potential reviewers. The reviewers may form a pool of individuals that are qualified to perform an assessment task, such as reviewing documentation and providing a judgment regarding the content of the documentation, such as whether a patient described in the documentation is of a particular health status. The reviewer database 127 may associate each reviewer with credential information, such as the reviewer's resume, job history, degrees, title, social networking information, etc.

The user device 130 may be an end-user computing device (e.g., a desktop or laptop computer, mobile device, etc.). The user device 130 may communicate with the assignment system 110 in relation to, for example, the assignment of tasks and the receipt of results of completed tasks. The user device 130 may generate the reviewer interface 135 which may enable the reviewer to receive and view the assigned task and provide a requested result.

The network 140 may be a local or global network and may include wired and/or wireless components and functionality which enable internal and/or external communication for components of the healthcare data environment 100. The network 140 may be embodied by the Internet, provided at least in part via cloud services, and/or may include one or more communication devices or systems which enable data transfer to and from the systems and components of the healthcare data environment 100.

In accordance with some exemplary embodiments, the assignment system 110, data source(s) 120, user device 130, or the related components include logic implemented in specialized hardware, software executed on hardware, or any combination of specialized hardware and software executed on hardware, for implementing the healthcare data environment 100 or related components. In some exemplary embodiments, the assignment system 110 or any of its components may be or include the IBM Watson™ system available from International Business Machines Corporation of Armonk, N.Y., which is augmented with the mechanisms of the illustrative embodiments described hereafter.

Figure 2:
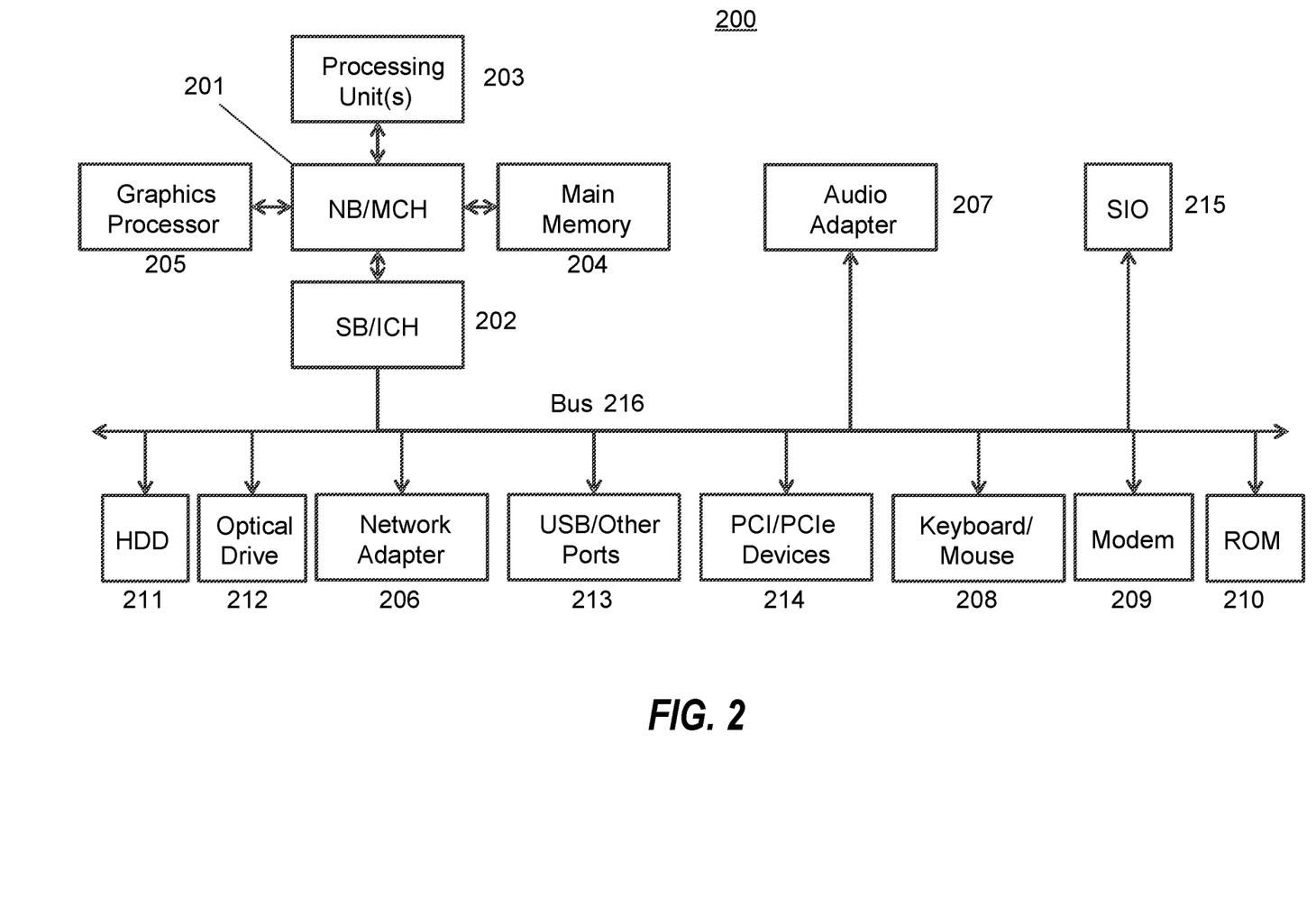
FIG. 2 is a block diagram of an example data processing system in which aspects of the illustrative embodiments are implemented.

FIG. 2 is a block diagram of an example data processing system 200 in which aspects of the illustrative embodiments may be implemented. Data processing system 200 is an example of a computer in which computer usable code or instructions implementing the process for illustrative embodiments of the present invention are located. In one embodiment, the data processing system 200 represents one or more of the assignment system 110, the one or more data sources 120, or the user device 130, and implements at least some of the functional aspects described herein.

In the depicted example, data processing system 200 can employ a hub architecture including a north bridge and memory controller hub (NB/MCH) 201 and south bridge and input/output (I/O) controller hub (SB/ICH) 202. Processing unit 203, main memory 204, and graphics processor 205 can be connected to the NB/MCH 201. Graphics processor 205 can be connected to the NB/MCH 201 through an accelerated graphics port (AGP).

In the depicted example, the network adapter 206 connects to the SB/ICH 202. The audio adapter 207, keyboard and mouse adapter 208, modem 209, read only memory (ROM) 210, hard disk drive (HDD) 211, optical drive (CD or DVD) 212, universal serial bus (USB) ports and other communication ports 213, and the PCI/PCIe devices 214 can connect to the SB/ICH 202 through bus system 216. PCI/PCIe devices 214 may include Ethernet adapters, add-in cards, and PC cards for notebook computers. ROM 210 may be, for example, a flash basic input/output system (BIOS). The HDD 211 and optical drive 212 can use an integrated drive electronics (IDE) or serial advanced technology attachment (SATA) interface. The super I/O (SIO) device 215 can be connected to the SB/ICH 202.

An operating system can run on processing unit 203. The operating system can coordinate and provide control of various components within the data processing system 200. As a client, the operating system can be a commercially available operating system. An object-oriented programming system, such as the Java™ programming system, may run in conjunction with the operating system and provide calls to the operating system from the object-oriented programs or applications executing on the data processing system 200. As a server, the data processing system 200 can be an IBM® eServer™ System p® running the Advanced Interactive Executive operating system or the Linux operating system. The data processing system 200 can be a symmetric multiprocessor (SMP) system that can include a plurality of processors in the processing unit 203. Alternatively, a single processor system may be employed.

Instructions for the operating system, the object-oriented programming system, and applications or programs are located on storage devices, such as the HDD 211, and are loaded into the main memory 204 for execution by the processing unit 203. The processes for embodiments of the website navigation system can be performed by the processing unit 203 using computer usable program code, which can be located in a memory such as, for example, main memory 204, ROM 210, or in one or more peripheral devices.

A bus system 216 can be comprised of one or more busses. The bus system 216 can be implemented using any type of communication fabric or architecture that can provide for a transfer of data between different components or devices attached to the fabric or architecture. A communication unit such as the modem 209 or network adapter 206 can include one or more devices that can be used to transmit and receive data.

Those of ordinary skill in the art will appreciate that the hardware depicted in FIG. 2 may vary depending on the implementation. For example, the data processing system 200 includes several components which would not be directly included in some embodiments of the assignment system 110, data source(s) 120, or user device 130.

Moreover, other internal hardware or peripheral devices, such as flash memory, equivalent non-volatile memory, or optical disk drives may be used in addition to or in place of the hardware depicted. Moreover, the data processing system 200 can take the form of any of a number of different data processing systems, including but not limited to, client computing devices, server computing devices, tablet computers, laptop computers, telephone or other communication devices, personal digital assistants, and the like. Essentially, data processing system 200 can be any known or later developed data processing system without architectural limitation.

Figure 3:
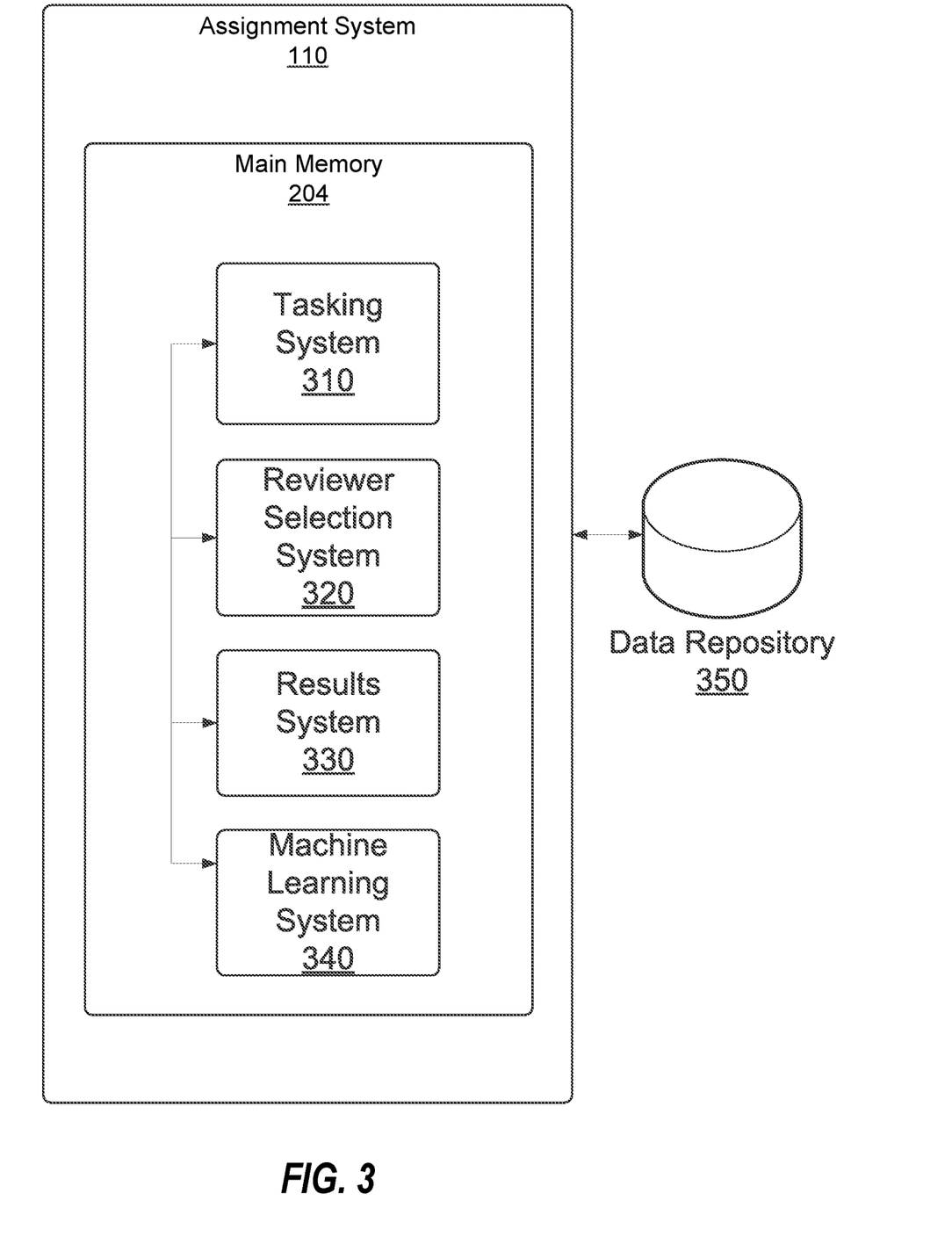
FIG. 3 is a block diagram of an example assignment system, according to an embodiment.

FIG. 3 illustrates an exemplary embodiment of the assignment system 110. In an exemplary embodiment, the assignment system 110 includes a tasking system 310, a reviewer selection system 320, a results system 330, and a machine learning system 340. These subsystems of the assignment system 110 may be components of a single device, or may be separated devices connected to each other (e.g., via the network 140). In some embodiments, the assignment system 110 may further include and/or be connected to a data repository 350.

The tasking system 310 may be a computing device or component (e.g., software or hardware engine or module) configured to determine one or more tasks associated with documents containing medical patient data. For example, the tasking system 310 may determine that one hundred clinical narrative notes in electronic patient charts require classification for a particular medical condition, such as whether or not the medical chart indicates that the patient's heart status is compensated or decompensated. In some embodiments, the task may include task criteria. For example, the task may include a threshold set of qualifications for a reviewer. In another example, the tasking system 310 may be configured to process the documents containing the medical data and extract criteria for the task. For instance, the tasking system 310 may perform natural language processing of the documents to extract relevant topics to determine a necessary background for a reviewer to complete a task of analyzing the document.

The reviewer selection system 320 may be a computing device or component (e.g., software or hardware engine or module) configured to select one or more reviewers from a pool in the reviewer database 127. For example, the reviewer selection system 320 may analyze the tasks to be completed and select one or more qualified individuals for completing the tasks. For instance, the reviewer selection system 320 may compare task criteria to stored credentials to determine one or more reviewers that are qualified to complete the task.

The tasking system 310 and/or reviewer selection system 320 may be further configured to communicate with the user device 130 in order to provide and receive information useful in determining a task, selecting reviewers, and providing task information to selected reviewers. For example, the reviewer interface 135 may include prompts for a user to provide information about a desired machine learning classifier that requires manual review of documents to help establish a ground truth. In this example, the tasking system 310 may be configured to determine one or more tasks that need to be completed (e.g., documents that need classified by a manual review) based on the requested information. In another example, the reviewer interface 135 may prompt a user to provide credential information, such as name, username/password, area of expertise, etc. In a further example, the reviewer interface 135 may provide a user with details about a task to be completed, such as the classification to be made and copies of the documents to be reviewed.

The results system 330 may be a computing device or component (e.g., software or hardware engine or module) configured to gather and store results of assigned assessment tasks. For instance, the results system 330 may collect results of completed tasks from a plurality of user devices 130 associated with different reviewers. The results system 330 may be configured to check the content and format of the result and determine whether the result is acceptable or whether additional information is necessary. For example, the results system 330 may determine whether a classification provided by a user device 130 satisfies a request task of providing a medical classification. The results system 330 may store the results in, for example, EMRs associated documents that were reviewed during the tasks.

The machine learning system 340 may be a computing device or component (e.g., software or hardware engine or module) configured to use results of assigned tasks to generate a machine learning algorithm. For example, the machine learning system 340 may review EMRs, including classification results from assessment tasks, in the medical records database 125 and use supervised or unsupervised learning to develop classifiers for medical conditions. In one example, the machine learning system 340 may be configured to generate a machine learning algorithm configured to classify a heart health status of a patient based on classifications provided by a reviewer (e.g., compensated or decompensated). The classifications from the reviewers may assist in establishing a ground truth for the algorithm training process.

The data repository 350 may be a database configured to store data. The data repository 350 may be configured to receive data from the assignment system 110 and/or from one or more data sources 120 and store the data according to appropriate storage protocols. In some embodiments, the data repository 350 receives data from the assignment system 110, such as from the tasking system 310 in order to improve the dataset usable by the machine learning system 340 for developing a classifier. In other embodiments, the data repository 350 receives data from the one or more data sources 120 and is a data supply for the assignment system 110.

Figure 4:
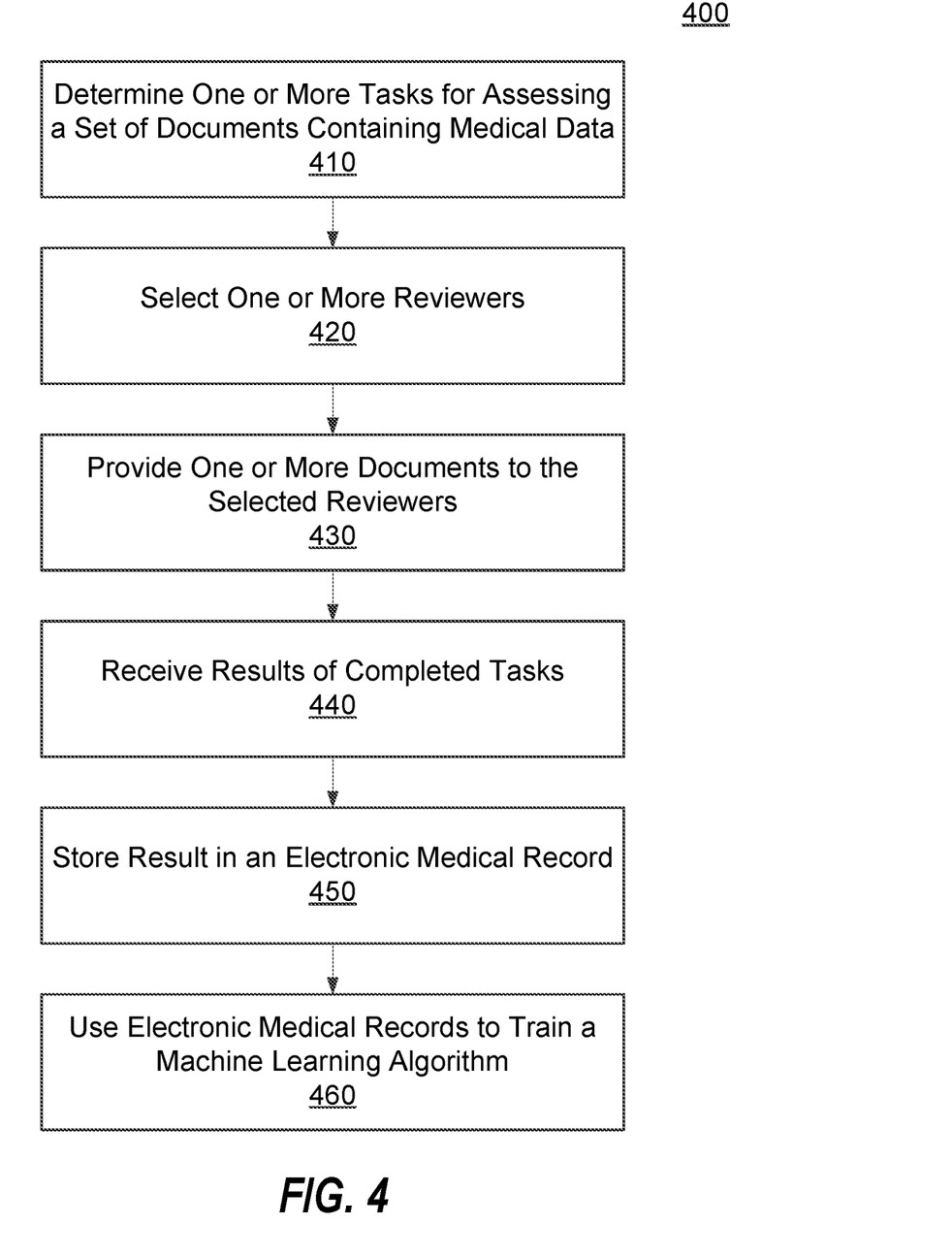
FIG. 4 is a flowchart of an example task assignment process, according to an embodiment.

FIG. 4 is a flowchart of an exemplary task assignment process 400. The assignment system 110 may perform one or more steps of the process 400 in order to facilitate manual review of one or more documents containing patient medical data.

In step 410, the assignment system 110 may determine one or more tasks for assessing a set of documents containing medical data. For example, the tasking system 310 may receive a request for classification of a medical condition for a set of documents having medical patient data. The tasking system 310 may receive an identification of the set of documents in the medical records database 125 in need of review, may identify the documents based on a filter or search function, and/or may receive the documents containing medical data as part of a task request. The tasking system 310 may further organize tasks by a project number to ensure that related data is maintained together.

In one example, the task request may include a label that is sought in EMRs of selected patients for performing machine learning on the records while accounting for the label. The request may further include possible values for the label. In one example, the task request may be for a determination of whether a patient has insomnia (label), with possible values for the result being "Has Condition" or "Does Not Have Condition" (label values). In another example, the task may be to determine a condition of a congestive heart failure (CHF) patient's heart (label), with the result being either compensated, decompensated, or indeterminate (label values). In some instances, a task request may include a need for a determination of multiple labels. For example, the task may require a reviewer to complete a checklist of conditions (e.g., yes or no reply for has or does not have a condition) for a given document containing medical patient data.

In some instances, the determined task may include task criteria, such as a threshold for credentials of a reviewer. For instance, a task for evaluating a non-specific health condition may require any physician to review. In another example, a task for comprehensively evaluating a heart health condition may require a cardiologist to review. In yet another example, a task for determining whether a blood pressure reading (or other test result) is present in the document may not have any credential requirements.

In step 420, the assignment system 110 may select one or more reviewers for completing the determined tasks. For example, the reviewer selection system 320 may select one or more reviewers from a pool in the reviewer database 127. In some embodiments, the reviewer selection system 320 may select one or more reviewers based on task criteria and credentials of the reviewers. For example, the reviewer selection system 320 may determine a subset of reviewers in the reviewer database 127 having credentials that exceed a threshold established by the task criteria and allocate documents for review to these reviewers. In some embodiments, the reviewer selection system 320 may evenly divide the documents between the selected reviewers. In another example, the reviewer selection system 320 may unevenly distribute the documents, such as by providing more documents to the most qualified reviewers.

In step 430, the assignment system 110 provides the one or more documents to the selected reviewers for completing the task. For instance, the assignment system 110 may use stored information in the reviewer database 127 to deliver the documents to a user device 130 associated with a respective reviewer. For example, the documents may be sent via email or through a portal as part of a software program. Each user device 130 may be configured to display the documents (or information for obtaining the documents) through the reviewer interface 135. The user device 130 may also receive task instruction information (e.g., the task that is being requested of the reviewer) and display this information through the reviewer interface 135.

In step 440, the assignment system 110 receives results of the completed tasks. For example, the results system 330 may collect information that is returned from the user devices 130 through the reviewer interface 135. For example, the results system 330 may include a label value associated with a document containing medical patient data (e.g., indicating that the reviewer determined that the document indicates that the patient does or does not have a certain condition based on the information in the document). The results system 330 may collect and organize results based on related tasks (e.g., by associating a result with a project identifier).

In step 450, the assignment system 110 stores the results in EMRs. For example, the results system 330 may update the EMR having the reviewed document to include a classification or label provided as a result of the assigned assessment task. In this way, the EMR may be enhanced based on the manual review of the medical patient data and completion of the assessment task by a qualified reviewer. In some embodiments, the results system 330 may determine a weighting for each result based on the credentials of the reviewer. For example, the review of a cardiologist may be given a greater weight than the review of a physician of another specialty when the task is heart-related.

In step 460, the assignment system 110 may optionally use the EMRs, including the received result of the task, to train a machine learning algorithm. For example, the machine learning system 340 may use classifications or labels determined as a result of assigned assessment tasks, alone or in combination with other data in the EMRs, to train a classifier for automatically labeling or classifying patient as having or not having a medical condition. In some embodiments, the machine learning system 340 may use weightings of the results in the training of the algorithm.

Some disclosed embodiments provide a system for assigning manual tasks in an efficient and effective manner by accounting for the requirements of the task and identifying individuals that are suited to reliably complete the task. Some embodiments provide a source for reliable subjective medical classifications that are needed to enhance medical systems, such as machine learning algorithms trained on ground truth. Some disclosed embodiments are configured to select appropriate reviewers and weight reviewer results based on available credential information. As a result, the disclosed embodiments are configured to produce reliable additions to valuable EMRs and facilitate the additions in a manner that is convenient to the reviewer.

The present description and claims may make use of the terms "a," "at least one of," and "one or more of," with regard to particular features and elements of the illustrative embodiments. It should be appreciated that these terms and phrases are intended to state that there is at least one of the particular features or elements present in the particular illustrative embodiment, but that more than one can also be present. That is, these terms/phrases are not intended to limit the description or claims to a single feature/element being present or require that a plurality of such features/elements be present. On the contrary, these terms/phrases only require at least a single feature/element with the possibility of a plurality of such features/elements being within the scope of the description and claims.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples are intended to be non-limiting and are not exhaustive of the various possibilities for implementing the mechanisms of the illustrative embodiments. It will be apparent to those of ordinary skill in the art in view of the present description, that there are many other alternative implementations for these various elements that may be utilized in addition to, or in replacement of, the example provided herein without departing from the spirit and scope of the present invention.

The system and processes of the Figures are not exclusive. Other systems, processes and menus may be derived in accordance with the principles of embodiments described herein to accomplish the same objectives. It is to be understood that the embodiments and variations shown and described herein are for illustration purposes only. Modifications to the current design may be implemented by those skilled in the art, without departing from the scope of the embodiments. As described herein, the various systems, subsystems, agents, managers, and processes can be implemented using hardware components, software components, and/or combinations thereof. No claim element herein is to be construed under the provisions of 35 U.S.C. 112, sixth paragraph, unless the element is expressly recited using the phrase "means for."

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

What is claimed is:

1. A computer-implemented method for training a machine learning algorithm to automatically classify documents containing medical patient data for a medical condition of interest comprising a processing device and a memory comprising instructions which are executed by the processor, the method comprising:
   collecting a first set of documents containing medical patient data from a database;
   training the machine learning algorithm using the first set of documents;
   collecting a second set of documents containing medical patient data from the database;
   assigning a label value to each of documents of the second set of documents, wherein the label value describes an applicability of the medical condition of interest to the document, wherein the assigning the label value comprises:
      determining one or more tasks for assessing the second set of documents containing medical patient data;
      selecting one or more reviewers based on the one or more tasks;
      providing one or more documents from the set second of documents to each of the selected one or more reviewers for completion of the one or more tasks;
      receiving a label value after completion of the one or more tasks by the selected one or more reviewers;
      assigning to the label value a confidence score, wherein the confidence score is representative of a degree of matching between the label value's subject matter and credential of a source of the label value such that a better degree of matching yields a better confidence score;
      establishing as ground truth for training the machine learning algorithm the one or more of the one or more documents to which the label value was assigned, the label value assigned to the one or more of the one or more documents, and, the confidence score assigned to the label value; and
   training the machine learning algorithm using the ground truth.

2. The method of claim 1, wherein determining one or more tasks comprises receiving a task request for the second set of documents containing medical patient data.

3. The method of claim 2, wherein the task request comprises task criteria.

4. The method of claim 2, wherein the task request includes a classification or label for the second set of documents containing medical patient data.

5. The method of claim 1, wherein providing the one or more documents comprises providing the one or more documents to a reviewer interface of a user device.

6. The method of claim 5, wherein providing the one or more documents comprises providing a task to the reviewer interface of the user device.

7. The method of claim 1, wherein providing the one or more documents comprises unevenly distributing the one or more documents of the second set of documents based on the credentials of the reviewers.

8. The method of claim 1, further comprising determining whether the result is acceptable based on the content and format of the result.

9. The method of claim 3, wherein selecting the one or more reviewers comprises comparing reviewer credentials to the task criteria and selecting one or more reviewers having credentials satisfying the task criteria.

10. The method of claim 3, wherein the task criteria comprises requirements for a reviewer's credentials.

11. The method of claim 1, wherein the confidence value is better when the source of the label value is a cardiologist when the label value's subject matter is a medical condition affecting a heart.

12. A ground truth generating system for generating ground truths for training a machine learning algorithm to automatically classify documents containing patient medical data for a medical condition of interest, comprising:
   a tasking system configured to:
      collect a first set of documents containing medical patient data, collect a second set of documents containing medical patient data from a database, and
      receive a task request for the review of the second set of documents containing patient medical data, the task request including a task to label the documents containing patient medical data and acceptable label values;
   a reviewer selection system configured to select one or more reviewers from a pool of reviewers to complete the task and provide one or more documents from the second set of documents to each of the selected one or more reviewers for completion of the task;

a results system configured to:
    receive a label value after completion of the one or more tasks by the selected one or more reviewers and store the result in an electronic medical record database, wherein the label value describes an applicability of the medical condition of interest to the reviewed one or more documents, and
    assign to the label value a confidence score, wherein the confidence score is representative of a degree of matching between the label value's subject matter and credentials of the selected one or more reviewer who provided the result such that a better degree of matching yields a better confidence score; and
a machine learning system configured to:
    train the machine learning algorithm using the first set of documents,
    establish as ground truth the reviewed one or more documents, the label value, and the confidence score assigned to the label value, and
    train the machine learning algorithm using the ground truth.

13. The system of claim 12, wherein the task request comprises task criteria.

14. The system of claim 13, wherein the task criteria comprises requirements for a reviewer's credentials.

15. The system of claim 13, wherein selecting the one or more reviewers comprises comparing reviewer credentials to the task criteria and selecting one or more reviewers having credentials satisfying the task criteria.

16. The system of claim 12, wherein providing the one or more documents comprises providing the one or more documents to a reviewer interface of a user device.

17. The system of claim 16, wherein providing the one or more documents comprises providing a task to the reviewer interface of the user device.

18. The system of claim 12, wherein providing the one or more documents comprises unevenly distributing the documents of the set of documents based on the credentials of the reviewers.

19. A computer program product for generating ground truths for training a machine learning algorithm to automatically classify documents containing medical patient data for a medical condition of interest, the computer program product comprising a computer readable storage medium having program instructions embodied therewith, the program instructions executable by a processor to cause the processor to:
    collect a first set of documents containing medical patient data from a database;
    train the machine learning algorithm using the first set of documents;
    collect a second set of documents containing medical patient data from a database;
    assign a label value to each of documents of the second set of documents, wherein the label value describes an applicability of the medical condition of interest to the document, wherein the assigning the label value comprises:
        determining one or more tasks for assessing a set of documents containing medical patient data;
        selecting one or more reviewers based on the one or more tasks;
        providing one or more documents from the set of documents to each of the selected one or more reviewers for completion of the one or more tasks;
        receiving a label value after completion of the one or more tasks by the selected one or more reviewers;
    assign to the label value a confidence score, wherein the confidence score is representative of a degree of matching between the label value's subject matter and credential of a source of the label value such that a better degree of matching yields a better confidence score;
    establishing as ground truth for training the machine learning algorithm the one or more of the one or more documents to which the label value was assigned, the label value assigned to the one or more of the one or more documents, and, the confidence score assigned to the label value; and
    training the machine learning algorithm based on the ground truth.

* * * * *